United States Patent [19]

Coates et al.

[11] Patent Number: 5,762,063

[45] Date of Patent: Jun. 9, 1998

[54] BAG-VALVE-MASK RESUSCITATOR ATTACHMENT HAVING SYRINGE AND NEBULIZER INJECTION PORTS

[76] Inventors: Michael R. Coates; Donna F. Coates, both of 5404-80th Ave. Cir. E. Palmetto, Fla. 34221

[21] Appl. No.: 861,145

[22] Filed: May 21, 1997

[51] Int. Cl.[6] ............................. A62B 9/04; A61M 16/10
[52] U.S. Cl. ..................... 128/205.13; 128/202.27; 128/203.12; 128/207.16; 128/205.17
[58] Field of Search .................... 128/202.28–203.12, 128/205.13–205.17, 205.24, 205.26, 204.18, 207.15, 207.16, 203.28, 202.27

[56] References Cited

U.S. PATENT DOCUMENTS

| | | | |
|---|---|---|---|
| 4,240,417 | 12/1980 | Holever | 128/203.12 |
| 4,320,754 | 3/1982 | Watson et al. | 128/204.25 |
| 4,865,027 | 9/1989 | Laanen et al. | 128/200.21 |
| 4,953,547 | 9/1990 | Poole, Jr. | 128/203.12 |
| 5,181,508 | 1/1993 | Poole, Jr. | 128/203.12 |
| 5,329,921 | 7/1994 | Socaris et al. | 128/203.12 |
| 5,359,998 | 11/1994 | Lloyd | 128/203.11 |
| 5,443,059 | 8/1995 | Koch et al. | 128/203.12 |
| 5,485,835 | 1/1996 | Vande Streek et al. | 128/205.13 |
| 5,613,489 | 3/1997 | Miller et al. | 128/203.28 |
| 5,701,886 | 12/1997 | Ryatt | 128/203.12 |

*Primary Examiner*—Kimberly L. Asher
*Attorney, Agent, or Firm*—Dorothy S. Morse

[57] ABSTRACT

A medication introducing device for airtight connection between a bag-valve mask apparatus, or other similar pre-hospital emergency respiratory device, and an endo-tracheal tube installed in a patient, the device comprising a central housing having a top opening, a bottom opening, and a minimum of two medication administering ports, at least one of the ports being an injection port for emergency administering of medications through pre-filled syringes into patients for which an intravenous line cannot be established, medications such as cardiac medications including atropine, epinephrine, lidocaine, and narcan, and at least one port being a nebulizer port for administering asthma medications to an intubated patient undergoing pre-hospital emergency CPR. It is contemplated for the present invention to be made from chemically inert materials, to have a sufficiently low manufacturing cost so that it can be disposable, and for each port to have an airtight end cap. Applications may include, but are not limited to, pre-hospital emergency and rescue situations in which a bag-valve mask apparatus must be used on an intubated patient.

11 Claims, 1 Drawing Sheet

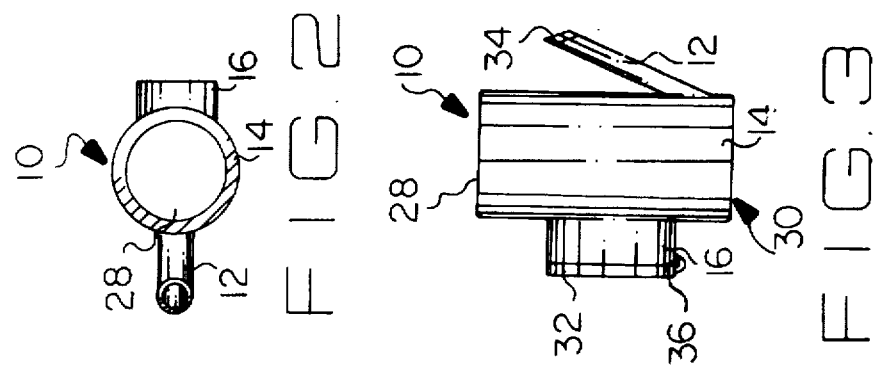
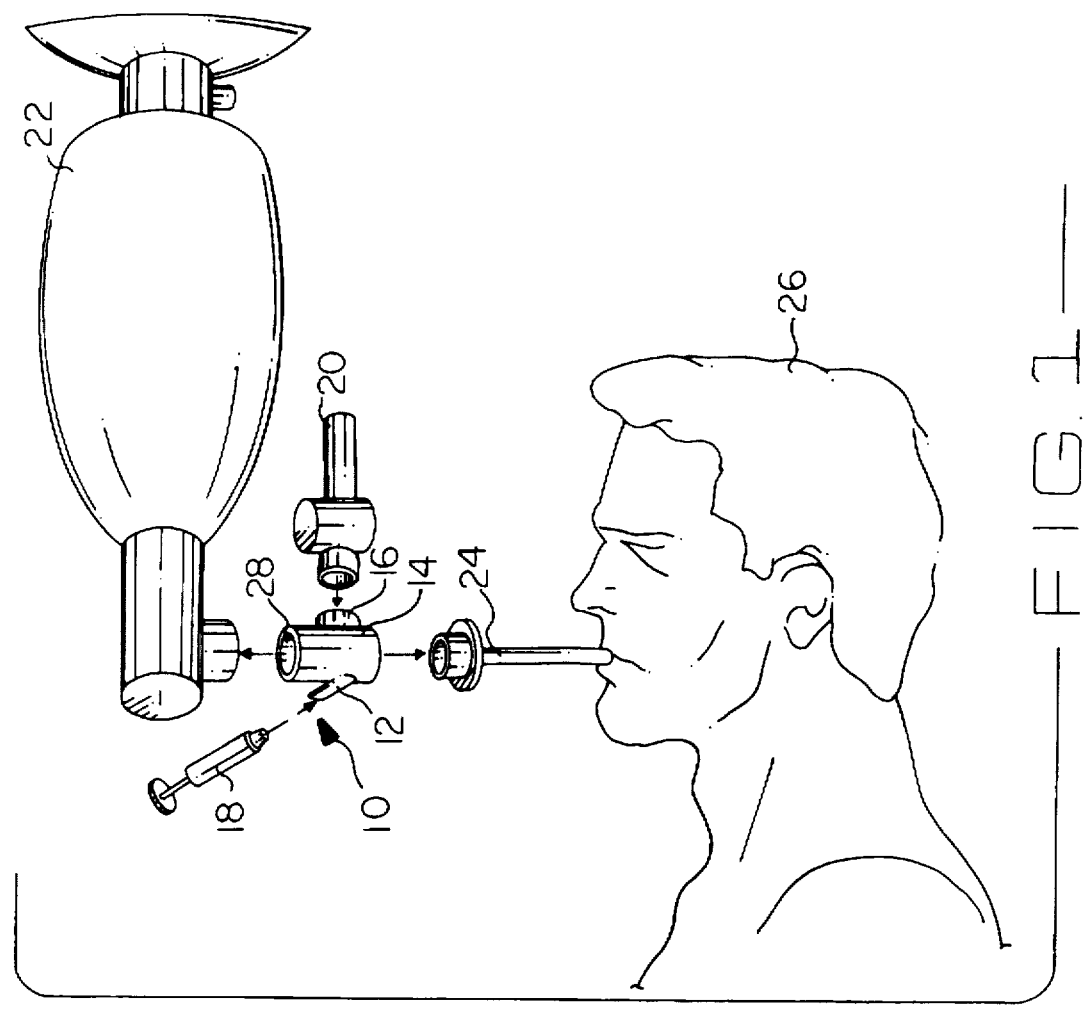

BAG-VALVE-MASK RESUSCITATOR ATTACHMENT HAVING SYRINGE AND NEBULIZER INJECTION PORTS

BACKGROUND—FIELD OF INVENTION

This invention relates to adapters and other devices for use with pre-hospital respiratory assist equipment, specifically to a device for use with the type of bag-valve mask apparatus commonly used for pre-hospital emergency respiratory assistance when CPR must be given to an intubated patient, the device comprising a central housing having an upper opening dimensioned for airtight connection to the bag-valve mask apparatus, a lower opening dimensioned for airtight connection to the endo-tracheal tube, and a minimum of two laterally positioned ports therethrough, at least one port being a syringe injection port for the emergency administering of medications, such as cardiac medications, into patients for whom intravenous injection cannot be established, and at least one port being a nebulizer port for administering asthma medications to intubated patients while they are undergoing CPR. Applications may include, but are not limited to, emergency and rescue situations in which a bag-valve mask apparatus is used on an intubated patient so that CPR won't have to be interrupted to administer medications to such patients.

BACKGROUND—DESCRIPTION OF PRIOR ART

In emergency and rescue situations which necessitate cardiac pulmonary resuscitation (CPR), it is common for patients to require medications, such as cardiac medications, and for such medications to be administered through the use of an intravenous line. However, establishing an intravenous line can be difficult and time consuming in some patients. For example, this can be due to the type of injury sustained by the patient, obesity, diabetes, as well as many other factors. When an intravenous line cannot be attempted or the establishment of an intravenous line has been attempted and failed, emergency medical personnel must look for alternative ways in which to administer the medications indicated by the patient's condition.

A secondary approved method for administering medications to a patient can be performed through the trachea which allows the medications to be absorbed into the bloodstream through the lungs. By using a syringe medications are injected into an endo-tracheal tube which is placed through the mouth and connects with the patient's trachea. However, when the type of bag-valve mask apparatus commonly used for pre-hospital CPR is connected to the endo-tracheal tube, CPR must be interrupted to administer the medications to the patient by this secondary method at a risk to the patient.

When encountering a patient requiring CPR in a pre-hospital situation, one of the first things that emergency medical personnel are known do is to intubate the patient by placing a plastic tube into the patient's trachea. The endo-tracheal tube maintains the trachea in an open condition and provides a conduit for administering medications. However, prior to injecting medications into the tube through pre-filled syringes, CPR must be stopped, the bag-valve mask apparatus or other type of pre-hospital artificial respiratory assist device, must be disconnected from the endo-tracheal tube, and the medication must be injected into the tube, after which the artificial respiratory assist device must be reattached to the endo-tracheal tube before CPR can be resumed. Disadvantages of this procedure involve both the risks associated with the interruption of CPR, as well as the risk of dislodging the endo-tracheal tube during the disconnection and reconnection of the artificial respiratory assist device.

In addition, pre-hospital emergency medical personnel also often encounter asthmatic patients who require endo-tracheal intubation and artificial respiration. Such patients are at an extreme disadvantage since there are no pre-hospital artificial respiration i devices currently available to rescue workers for providing nebulized asthma medication to them. Again, as with the administering of injected medications, when a bag-valve mask apparatus, or similar pre-hospital respiratory assistance device is used with an intubated patient, the artificial respiratory process must be interrupted at risk to the patient when the patient's condition indicates the need for administering nebulized asthma medication. It is not known to have a device for use with the type of bag-valve mask apparatus commonly used for pre-hospital emergency respiratory assistance during CPR, the device configured for airtight connection between the bag-valve mask apparatus and the upper portion of the endo-tracheal tube inserted into a patient for maintaining the trachea in an open position, and comprising a central housing having an upper opening dimensioned for connection to the bag-valve mask apparatus, a lower opening dimensioned for connection to the endo-tracheal tube, and a minimum of two ports laterally positioned through the central housing, at least one of the ports being a syringe injection port for the emergency administering of medications into patients for whom intravenous lines could not be established, such as for administering cardiac medications including atropine, epinephrine, lidocaine, and narcan to a patient during CPR, and at least one nebulizer port for administering asthma medications during CPR so that the bag-valve mask apparatus does not have to be disconnected from the endo-tracheal tube and CPR thereby discontinued during the administering of such medications during pre-hospital emergency care.

Prior art devices are known for use in delivering aerosols to human and veterinary patients through endo-tracheal tubes, and the present invention can be distinguished from them. Most prior art devices and systems related to aerosol use are configured for use in a hospital settings for continuous flow of aerosols to a patient, or involve quick-connect valves or locking connectors which prevent respiratory hoses from becoming disconnected during surgery. In contrast, the present invention is contemplated to be a low cost, disposable device which helps pre-hospital emergency medical personnel to quickly administer medications upon demand to a patient during the conduct of CPR and other patient stabilizing procedures. The main advantage of the present invention is as a time-saving device in life-threatening situations where every second of delay poses a risk to the patient. One example of a prior art device for introducing aerosols to a patient is the invention disclosed in U.S. Pat. No. 5,287,849 to Piper (1994), which comprises a medicinal aerosol delivery system for connection to a ventilator. As a patient attached to the Piper invention inhales, a fine aerosol is drawn into the patient's lungs, and during exhalation the charging volume is filled with aerosol for use during the next patient inhalation so that a continuous flow of aerosol can be administered to the patient. In contrast to the prior art, the present invention provides a simple, compact, lightweight, and disposable device with at least two medication introducing ports therethrough which can be made readily available to emergency medical personnel in pre-hospital rescue situations so that they can more quickly adapt to the changing needs of patients.

SUMMARY OF INVENTION—OBJECTS AND ADVANTAGES

It is the primary object of this invention to provide a means of administering medications by both injection and nebulization into an endo-tracheal tube positioned in the trachea of a patient undergoing CPR and whose endo-tracheal tube is connected to a bag-valve mask apparatus, or other similar pre-hospital emergency respiratory assistance device, so that the medication can move through the lungs and into the bloodstream without disconnection of the bag-valve mask apparatus and concomitant interruption of CPR. It is also an object of this invention to provide a means for pre-hospital emergency personnel to administer both cardiac medications, such as Atropine, Epinephrine, Lidocaine, and Narcan, and asthma medications, such as Proventil, and Isoetherine, to patients who require intubation without interruption of CPR. A further object of this invention is to provide a medication introducing device for use between a bag-valve mask apparatus and an endo-tracheal tube which is compact in size, and easy to connect between a bag-valve mask apparatus and an endo-tracheal tube for rapid installation and quick initiation of CPR. It is also an object of this invention to provide a medication introducing device for use between a bag-valve mask apparatus and an endo-tracheal tube which is made from materials that are chemically inert. A further object of this invention is to provide a medication introducing device which has airtight sealing means for connection for its medication introducing ports. It is also an object of this invention to provide a medication introducing device for use between a bag-valve mask apparatus and an endo-tracheal tube which is sufficiently low in cost to be disposable.

As described herein, properly manufactured and connected between a bag-valve is mask device, or similar pre-hospital emergency respiratory assistance device, and an endo-tracheal tube installed within a patient for maintaining the patient's trachea in an open position during emergency treatment, the present invention would provide pre-hospital emergency medical personnel with a means of administering injected and nebulized medications to the patient without the interruption of CPR. Currently such means are not available to pre-hospital emergency medical personnel and the bag-valve mask apparatus must be disconnected from the endo-tracheal tube should a patient's condition indicate a need for cardiac or asthma medication. Since intravenous lines cannot be established in many patients for the emergency administering of medications, alternative delivery means for such medications is required. The present invention provides a disposable, compact, easily handled, and inexpensively manufactured medication introducing device for administering of medication through the trachea, which is a secondary approved method for delivery of some medications. The present invention would have a central housing with a top opening configured for connection to the air exhaust tube of a pre-hospital bag-valve mask device, a bottom opening for connection to the upper portion of an endo-tracheal tube, and at least two ports laterally positioned through the central housing which communicate with the upper opening in the endo-tracheal tube. It is contemplated to have at least one port configured for injection of medications through pre-filled syringes, and at least one port configured for connection to the standard size of discharge opening commonly used in nebulizers for administering a fine mist of medication which can be rapidly absorbed into the respiratory tissue of asthma patients. It is contemplated for the housing and ports to be made from chemically inert materials and for each port to have an airtight end cap which can be tightly attached to it to seal it during CPR both before and after medication introduction into a patient. It is also contemplated for the present invention to be compact in configuration with the length of its ports sufficiently long for easy access thereto, but not excessively long that they become cumbersome and interfere with other emergency care procedures.

The description herein provides preferred embodiments of the present invention but should not be construed as limiting the scope of the respiratory assist device invention. For example, variations in the length of the central housing, the materials from which the central housing is made, the longitudinal dimension of the injection port and the nebulizer port, the materials from which the end caps are made, and the sealing means by which the end caps are attached to the ports, other than those shown and described herein, may be incorporated into the present invention. Thus the scope of the present invention should be determined by the appended claims and their legal equivalents, rather than the examples given.

BRIEF DESCRIPTION OF THE DRAWINGS

FIG. 1 is an exploded side view of the invention positioned for attachment between a bag-valve mask device and an endo-tracheal tube installed in a patient, and having a syringe and a nebulizer poised for administering medications into an injection port and a nebulizer port, respectively.

FIG. 2 is a top view of the invention having a nebulizer port and injection port laterally depending from opposed sides of a central housing.

FIG. 3 is a side view of the invention with a nebulizer port having a large end cap attached thereto and an injection port in an opposed position from the nebulizer port having a small end cap attached thereto.

DETAILED DESCRIPTION OF PREFERRED EMBODIMENTS

FIG. 1 shows a preferred embodiment of a pharmacological introducing respiratory assistance device 10 having a central housing 14, with a top opening 28 and a bottom opening, shown in FIG. 3 as number 30. In addition, FIG. 1 shows pharmacological introducing respiratory assistance device 10 having an injection port 12 depending laterally from central housing 14, and a nebulizer port 16 also depending laterally from central housing 14 in a position opposed to injection port 12. Although the number of injection ports 12 and nebulizer ports 16, and their placement, are not critical to the present invention, it is contemplated in the preferred embodiment to have one injection port 12 and one nebulizer port 16 placed in opposed positions for maximum convenience during use. FIG. 1 shows nebulizer port 16 being larger in diameter than injection port 12, and nebulizer port 16 being positioned approximately perpendicular in its connection to central housing 14. Although not shown, nebulizer port 16 has a hollow interior which communicates with the interior portion of central housing 14. Similarly, injection port 12 has a hollow interior which communicates with the interior portion of central housing 14. However, in the preferred embodiment it is contemplated for injection port 12 to have a narrower diameter than nebulizer port 16 to reduce the interior surface area available for adherence of medications, and for injection port 12 to be positioned at an oblique angle relative to central housing 14 with its lower end positioned below the lower end of nebulizer port 16 to provide the shortest distance possible for medications to travel to reach endo-tracheal tube 24 and to allow gravity to assist the maximum flow of medications from injection port 12 into patient 26. FIG. 1 also shows pharmacological introducing respiratory assistance device 10 poised for connection between a bag-valve mask device 22 positioned over a prone patient 26, and an endo-tracheal tube 24 upwardly depending from the mouth of patient 26. FIG. 1 also shows a syringe 18 and a nebulizer 20 poised for administering medications through injection port 12 and nebulizer port 16, respectively.

FIG. 2 shows nebulizer port 16 and injection port 12 laterally depending from opposed sides of central housing 14. FIG. 2 also shows top opening 28 contemplated for connection to bag-valve mask device 22. In FIG. 2, injection port 12 is shown to angle upwardly from central housing 14 so that gravity will help medications injected therein to move more rapidly downward into endo-tracheal tube 24 and into the lungs of patient 26.

FIG. 3 shows emergency respiratory assist device having nebulizer port 16 depending from one side of central housing 14 and injection port 12 depending from central housing 14 in a position opposed from the nebulizer port. FIG. 3 also shows nebulizer port 16 having a large end cap 32 attached thereto and injection port 12 having a small end cap 34 attached thereto. It is contemplated for large end cap 32 to attach to nebulizer port 16 and for small end cap 34 to attach to injection port 12 so as to each provide an air tight seal during CPR with the use of bag-valve mask devise 22 both before and after medication (not shown) introduction into patient 26. In the preferred embodiment it is contemplated for large end cap 32 to comprise a tight fitting snap-on cap or a threaded cap which prevents large end cap 32 from being forced off of the end of nebulizer port 16 due to the positive pressure generated by CPR. It is only critical that large end cap 32 be able to be easily removed and replaced by rescue workers for rapid initiation of CPR. In the preferred embodiment it is contemplated for small end cap 34 to comprise a plastic or rubber cap similar to the ports found on intravenous tubing which allow medication to be injected therethrough with a syringe and needle, the hole created thereby self-sealing after the needle is withdrawn to prevent air leakage. In addition, although not critical, it is contemplated for a connecting member 36 to be connected between large end cap 32 and nebulizer port 16 to retain end cap 32 close at hand when removed from nebulizer port 16. The materials from which connecting member 36 is made are not critical to the present invention. However, in the preferred embodiment, although not limited to the following, it is contemplated for connecting member 36 to be provided in the form of a plastic strap.

In the preferred embodiment of pharmacological introducing respiratory assistance device 10 it is contemplated for central housing 14, injection port 12, and nebulizer port 16 to be made as a one-piece unit of plastic materials, through molded construction. It is critical that pharmacological introducing respiratory assistance device 10, at a minimum, to be made from materials which are chemically inert to the types of cardiac and asthma medications commonly required for administering to patients undergoing CPR in pre-hospital emergency situations.

To use the pharmacological introducing respiratory assistance device 10, pre-hospital emergency personnel (not shown) would first intubate a prone patient 26. With endo-tracheal tube 24 upwardly depending from the mouth of patient 26, bag-valve mask device 22 would be positioned over patient 26 with its air exhaust tube pointed in the direction of patient 26. When CPR is required for patient 26, airtight connection of the present invention between the air exhaust tube of bag-valve mask 22 and the upper portion of endo-tracheal tube 24, would be made to position injection port 12 and nebulizer port 16 so that they are each easily accessible should the administering of medications (not shown) by injection or nebulization into the lungs of patient 26 be required during CPR. Use of nebulizer port 16 and injection port 12 allow introduction of medications into patient 26 without interruption of CPR and eliminate the risk of dislodging endo-tracheal tube 24 which formerly was required when the air exhaust tube of bag-valve mask device 22 was connected directly to endo-tracheal tube 24. After patient use, it is contemplated for pharmacological introducing respiratory assistance device 10 to be disposable. Large end cap 32 would be removed from nebulizer port 16, as needed for use, then replaced after use to provide an airtight connection for the continuation of CPR. Connecting member 36, if used, would retain large end cap 32 close at hand for prompt replacement so that CPR need not be interrupted.

What is claimed is:

1. A medication introducing device for connection between a bag-valve mask apparatus used for pre-hospital emergency respiratory assistance and the upper portion of an endo-tracheal tube in a patient undergoing CPR whose condition requires the administering of medications and when an intravenous line cannot be established in the patient, said device comprising a central housing having an upper opening configured for airtight connection to the bag-valve mask apparatus, a lower opening configured for airtight connection to the endo-tracheal tube, at least one injection port for the administering of liquid medications through use of syringes, and at least one nebulizer port for administering medications in the form of a mist, said injection port and said nebulizer port laterally depending from said central housing and each having a hollow interior communicating with said lower opening so that medications can be administered to the patient without disconnection of the bag-valve mask apparatus and the concomitant interruption of CPR.

2. The device of claim 1 wherein said injection port is positioned near to said lower opening and connected to said central housing at an oblique angle to minimize the amount of injected medication adhering to said injection port during use.

3. The device of claim 1 further comprising a plurality of end caps, one of said end caps configured for airtight sealing of said nebulizer port and one of said caps for sealing said injection port.

4. The device of claim 3 wherein one of said end caps is a snap-on type of cap configured for sealing said nebulizer port in an airtight and sufficiently secure manner to withstand the positive pressures generated by CPR.

5. The device of claim 3 wherein said injection port has an upper end, and wherein one of said end caps is a cap made of self-sealing material and having sufficient dimension to completely cover said upper end, said material is capable of self-sealing after each needle injection made to introduce medications into said injection port.

6. The device of claim 1 made as a one-piece unit from molded construction.

7. A medication introducing device for connection between a bag-valve mask apparatus used for pre-hospital emergency respiratory assistance and the upper portion of an endo-tracheal tube in a patient undergoing CPR whose condition requires the administering of medications and when an intravenous line cannot be established in the patient, said device comprising a central housing having an upper opening configured for airtight connection to the bag-valve mask apparatus, a lower opening configured for airtight connection to the endo-tracheal tube, at least one injection port for the administering of liquid medications through use of syringes, and at least one nebulizer port for administering medications in the form of a mist, said injection port and said nebulizer port laterally depending from said central housing and each having a hollow interior communicating with said lower opening so that medications can be administered to the patient without disconnection of the bag-valve mask apparatus and the concomitant interruption of CPR, said injection port also being positioned near to said lower opening and connected to said central housing at an oblique angle to minimize the amount of injected medication adhering to said injection port during use.

8. The device of claim 7 further comprising a plurality of end caps, one of said end caps configured for airtight sealing of said nebulizer port and one of said caps for sealing said injection port.

9. The device of claim 8 wherein one of said end caps is a snap-on type of cap configured for sealing said nebulizer port in an airtight and sufficiently secure manner to withstand the positive pressures generated by CPR.

10. The device of claim 8 wherein said injection port has an upper end, and wherein one of said end caps is a cap made of self-sealing material and having sufficient dimension to completely cover said upper end, said material is capable of self-sealing after each needle injection made to introduce medications into said injection port.

11. A medication introducing device for connection between a bag-valve mask apparatus used for pre-hospital emergency respiratory assistance and the upper portion of an endo-tracheal tube in a patient undergoing CPR whose condition requires the administering of medications and when an intravenous line cannot be established in the patient, said device comprising a central housing having an upper opening configured for airtight connection to the bag-valve mask apparatus, a lower opening configured for airtight connection to the endo-tracheal tube, at least one injection port for the administering of liquid medications through use of syringes, and at least one nebulizer port for administering medications in the form of a mist, said injection port and said nebulizer port laterally depending from said central housing and each having a hollow interior communicating with said lower opening so that medications can be administered to the patient without disconnection of the bag-valve mask apparatus and the concomitant interruption of CPR, said injection port also being positioned near to said lower opening and connected to said central housing at an oblique angle to minimize the amount of injected medication adhering to said injection port during use, further comprising a plurality of end caps, one of said end caps configured for airtight sealing of said nebulizer port and one of said caps for sealing said injection port, and wherein one of said end caps is a snap-on type of cap configured for sealing said nebulizer port in an airtight and sufficiently secure manner to withstand the positive pressures generated by CPR, and wherein said injection port has an upper end and one of said end caps is a cap made of self-sealing material and having sufficient dimension to completely cover said upper end, said material is capable of self-sealing after each needle injection made to introduce medications into said injection port.

* * * * *